(12) United States Patent
Minezaki

(10) Patent No.: US 6,890,320 B2
(45) Date of Patent: May 10, 2005

(54) CONTINUOUS LIQUID INFUSION DEVICE

(75) Inventor: Susumu Minezaki, Tokyo (JP)

(73) Assignee: Orchis Company Limited, Tokyo (JP)

( * ) Notice: Subject to any disclaimer, the term of this patent is extended or adjusted under 35 U.S.C. 154(b) by 143 days.

(21) Appl. No.: 10/321,551

(22) Filed: Dec. 18, 2002

(65) Prior Publication Data

US 2003/0120211 A1 Jun. 26, 2003

(30) Foreign Application Priority Data

Dec. 25, 2001 (JP) ........................................ 2001-392888

(51) Int. Cl.[7] ........................ A61M 37/00; A61M 5/315
(52) U.S. Cl. ...................... 604/143; 604/140; 604/141; 604/228
(58) Field of Search .......................... 604/70, 131, 140, 604/141, 143, 187, 207, 218, 220, 222, 227, 228, 236–238; 222/52, 57, 544

(56) References Cited

U.S. PATENT DOCUMENTS

| 4,036,232 A | * | 7/1977 | Genese ........................ 604/143 |
| 5,024,664 A | | 6/1991 | Mitchell |
| 6,139,530 A | * | 10/2000 | Hiejima et al. ............. 604/140 |

FOREIGN PATENT DOCUMENTS

| EP | 0 715 861 A1 | 6/1996 |
| JP | 5-509021 | 12/1993 |
| JP | 8-257119 | 10/1996 |
| JP | 0 945 150 A2 | 9/1999 |
| JP | 11-276581 | 10/1999 |
| JP | 2000-014776 | 1/2000 |
| JP | 3068265 | 2/2000 |
| JP | 2001-321438 | 11/2001 |
| JP | 2001-333980 | 12/2001 |
| WO | 715861 | 11/1995 |
| WO | 01/089610 | 11/2001 |

* cited by examiner

Primary Examiner—Brian L. Casler
Assistant Examiner—Catherine S. Williams
(74) Attorney, Agent, or Firm—Staas & Halsey LLP

(57) ABSTRACT

The invention provides a continuous liquid infusion device in which liquid syringe and a negative pressure cylinder are separable to use a liquid infused syringe. This continuous liquid infusion device includes: a negative pressure cylinder having a barrel part including an open/close valve at its tip and leg parts extending from a base end thereof; a piston air-tightly fitted in the barrel part and connected to a base end of an outer case covering an outer surface of the barrel part, through slots between the leg parts; a liquid syringe having a liquid infusion/discharge port at its tip, and a base end screwed with the outer case so that the liquid syringe is positioned back to back with the negative pressure cylinder; and a movable unit liquid-tightly fitted to an inner circumference of the tip of the liquid syringe and abutting against a base end of the leg parts.

3 Claims, 4 Drawing Sheets

FIG.3(a)
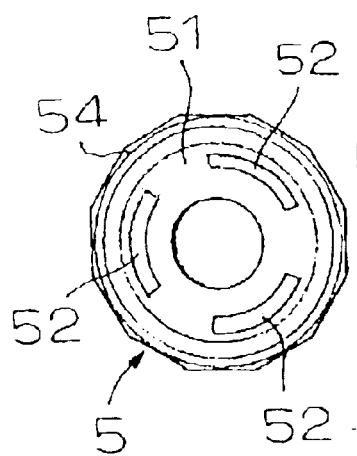
FIG.3(b) FIG.3(c) FIG.3(d)
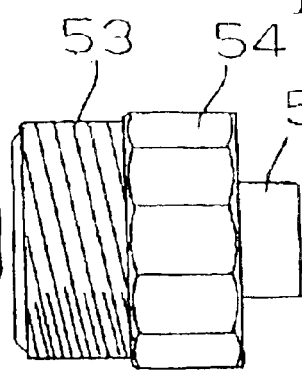
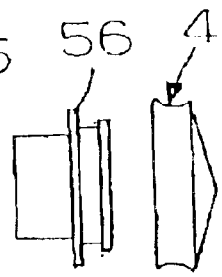
FIG.4
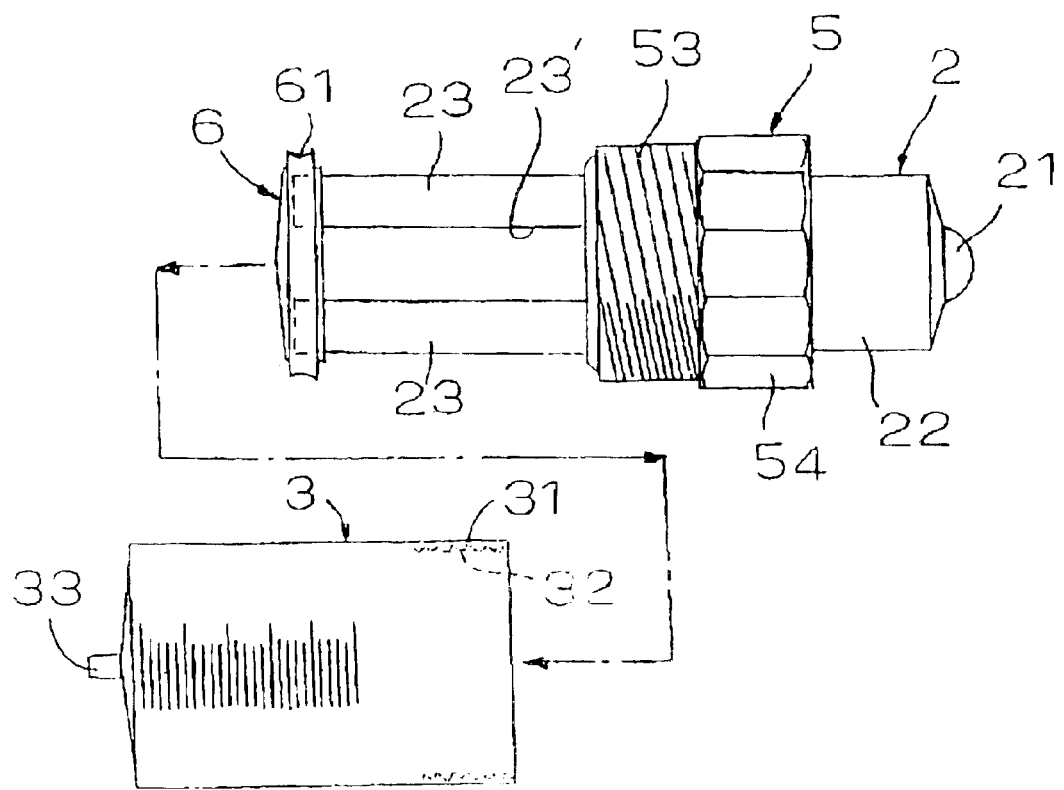

CONTINUOUS LIQUID INFUSION DEVICE

BACKGROUND OF THE INVENTION

1. Field of the Invention

The present invention relates to a continuous liquid infusion device for infusing transfusion liquid such as a nutrient solution and medicine such as an anti-cancer agent and an analgesic into a body at regular speed and flow rate.

2. Description of the Related Art

International Publication No. WO95/28977 discloses a typical conventional continuous liquid infusion device of this kind. This device has a structure in which liquid can be continuously infused by pressing a piston in a liquid syringe in synchronization with moving force of the piston which moves with use of a difference in pressure between a negative pressure space and atmospheric pressure, the negative pressure space being formed by a negative pressure cylinder and the piston air-tightly fitted into the negative pressure cylinder.

The conventional continuous liquid infusion device as described above requires two positions having large sliding resistance in the cylinder and the syringe in order to maintain air-tightness of the negative pressure cylinder, which causes difficulty in precise manufacturing as well as a disadvantage of poor operability in usage because large force is needed for infusing liquid.

Accordingly, the inventor of the present invention has disclosed a continuous liquid infusion device having excellent operability capable of infusing liquid with small force as Utility Model Registration No. 3068265 and Japanese Unexamined Patent Application Publication No. 2001-333980. The continuous liquid infusion device in these documents has the structure in which air-tightness between the negative pressure cylinder and the piston can be maintained at one position to reduce sliding resistance, and the liquid syringe and the negative pressure cylinder are separated so as to enable use of a liquid syringe into which liquid is infused in advance, reducing manufacturing costs and improving its operability and usability.

However, the inventor of the present invention has not been satisfied with the above techniques, further pursuing better manufacturability, reduction in the number of parts, shortening of the whole length, and the like to aggressively aim at development of a continuous liquid infusion device having further improved operability and usability with lowered manufacturing costs.

SUMMARY OF THE INVENTION

To solve the above problems, the present invention provides a disposable continuous liquid infusion device with a less number of parts and a shortened whole length, which realizes an easy-to-manufacture, easy-to-handle device with lowered manufacturing costs.

Further, another object is to provide a continuous liquid infusion device which has a liquid syringe and a negative pressure cylinder separated and enables use of a liquid syringe with liquid infused in advance therein.

In order to achieve the objects described above, the continuous liquid infusion device according to the present invention is characterized in that it comprises: a negative pressure cylinder having a barrel part with an open/close valve at its tip and leg parts extending from a base end of the barrel part; a piston air-tightly fitted in the barrel part of the negative pressure cylinder and connected to a base end of an outer case, which covers an outer surface of the barrel part, through slots between the leg parts of the negative pressure cylinder; a liquid syringe having a base end screwed with the outer case so that the liquid syringe is positioned back to back with the negative pressure cylinder, and a liquid infusion/discharge port at its tip; and a movable unit liquid-tightly fitted to an inner circumference of the tip of the liquid syringe and abutting against a base end of the leg parts of the negative pressure cylinder. In the continuous liquid infusion device the negative pressure cylinder moves by screwing the outer case to easily create an extra vacuum part (a spare pressure part for completely infusing liquid in the liquid syringe) in the negative pressure cylinder. Further, positioning the negative pressure cylinder and the liquid syringe back to back with each other reduces the number of the parts, achieving an excellent continuous liquid infusing function, shortening of the whole length, and advantageous operability and manufacturability.

Further, the continuous liquid infusion device according to the present invention is characterized in that the outer case is provided with an enlarged part as a handle in its outer circumference. It is structured to easily perform the screwing operation of the outer case for moving the negative pressure cylinder, which creates an extra vacuum part in the negative pressure cylinder.

Furthermore, the continuous liquid infusion device according to the present invention is characterized in that the liquid syringe is removable from the outer case and the negative pressure cylinder has a stopper for fixing a position where the negative pressure cylinder is moved in a negative pressure direction, which makes it possible to exchange the liquid syringe into a liquid syringe with liquid infused in advance therein, as necessary.

BRIEF DESCRIPTION OF THE DRAWINGS

The nature, principle, and utility of the invention will become more apparent from the following detailed description when read in conjunction with the accompanying drawings in which like parts are designated by identical reference numbers, in which:

FIG. 3(a) is a side view of an outer case seen from its base end face;

FIG. 3(b) is a front view of the outer case;

FIG. 3(c) is a front view of a piston supporting member;

FIG. 3(d) is a front view of a piston;

FIG. 4 is a front view showing a state in which the continuous liquid infusion device according to the one embodiment of the present invention is separated into a negative pressure cylinder and a liquid syringe;

DESCRIPTION OF THE PREFERRED EMBODIMENTS

Next, an embodiment of the present invention will be explained with reference to the attached drawings.

Figures 2A, 2B:
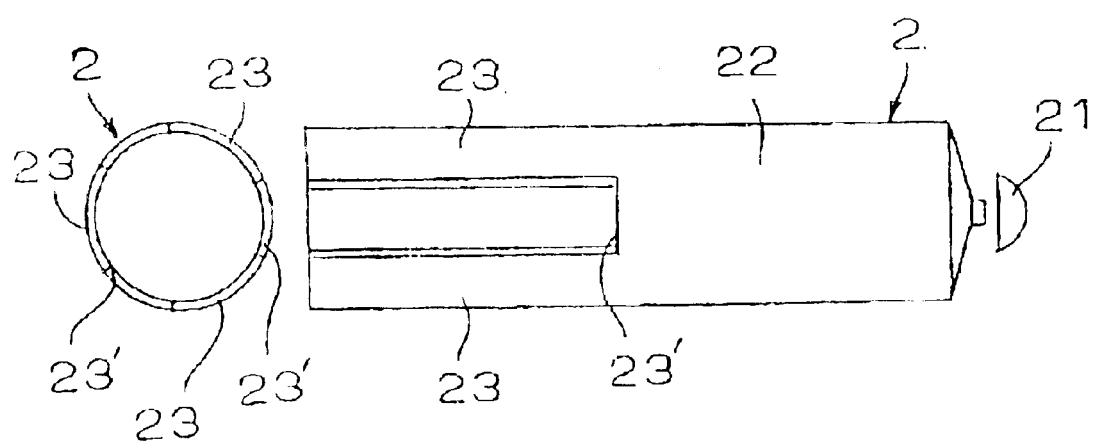
FIG. 2(a) is a side view of a negative pressure cylinder seen from its leg part side.
FIG. 2(b) is a front view of the negative pressure cylinder.

In the drawings, a continuous liquid infusion device according to one embodiment of the present invention is referenced to as number 1. In the continuous liquid infusion device 1, a negative pressure cylinder 2 and a liquid syringe 3 are positioned back to back. As shown in FIGS. 2(a) and 2(b), the negative pressure cylinder 2 has a barrel part 22 having an open/close valve 21 at its tip and leg parts 23 extending from a base end thereof. The base end of the barrel part 22 is equally divided into three (not limited to three), and the leg parts 23 extend from the three dividing positions with the same width in an axis direction. Between the leg parts 23 slits 23' are provided with the same width.

The open/close valve 21 provided at the tip of the negative pressure cylinder 2 is removed when a piston 4 is inserted into the barrel part 22 of the negative pressure cylinder 2 as will be described later. This is necessary to let the air out of the barrel part 22 to the atmosphere when the piston 4 is inserted from a base end of the negative pressure cylinder 2.

The piston 4 air-tightly fitted and inserted into the barrel part 22 of the negative pressure cylinder 2 is integrated with an outer case 5 covering an outer surface of the barrel part 22 of the negative pressure cylinder 2. In other words, a base end face 51 of the outer case 5 has through holes 52 through which the leg parts 23 of the negative pressure cylinder 2 pass as shown in FIG. 3(a).

As shown in FIG. 3(b), a male screw part 53 is provided to an outer circumference of the outer case 5 near the base end face 51. The male screw part 53 is screwed with a female screw part 32 provided on an inner surface of a base end 31 of the liquid syringe 3. Further, to an outer circumference of the outer case 5 near the tip, provided is an enlarged part (where a nut-like non-slip is formed) 54 as a handle to turn in a circumferential direction in order to fasten and loosen the outer case 5.

Furthermore, a barrel unit 55 (equivalent to a plunger) protrudes on an inner surface of the base end face 51 of the outer case 5, having a thickness thin enough to be loosely-fitted in the barrel part 22 of the negative pressure cylinder 2, a piston supporting member 56 is fitted and fixed to the barrel unit 55 as shown in FIG. 3(c), and the piston 4 shown in FIG. 3(d) can be fitted to the supporting member 56.

In order to combine the outer case 5 and the negative pressure cylinder 2, as described above, the piston 4 is fixed through the supporting member 56 to the tip of the barrel unit 55 protruding from the base end face 51 of the outer case 5, and the piston 4 is inserted into the barrel part 22 of the negative pressure cylinder 2. Before the insertion the open/close valve 21 provided at the tip is removed. Then, a base end of the leg parts 23 is made to pass through the through holes 52 provided on the base end face 51 of the outer case 5. Next, the male screw part 53 provided in the outer circumference of the outer case 5 is screwed with the female screw part 32 provided on the inner surface of the liquid syringe 3. Accordingly, the negative pressure cylinder 2 and the liquid syringe 3 are combined back to back. Incidentally, number 33 denotes a liquid infusion/discharge port provided at a tip of the liquid syringe 3.

A movable unit 6 is liquid-tightly fitted to an inner surface of the tip of the liquid syringe 3 through a gasket 61, and therefore the base end of the leg parts 23 of the negative pressure cylinder 2 abuts against the movable unit 6 when the outer case 5 is screwed with the liquid syringe 3. Incidentally, the base end of the leg parts 23 of the negative pressure cylinder 2 seems to be fixed to the movable unit 6 in FIG. 4, but the fixation is not always needed.

Figure 1:
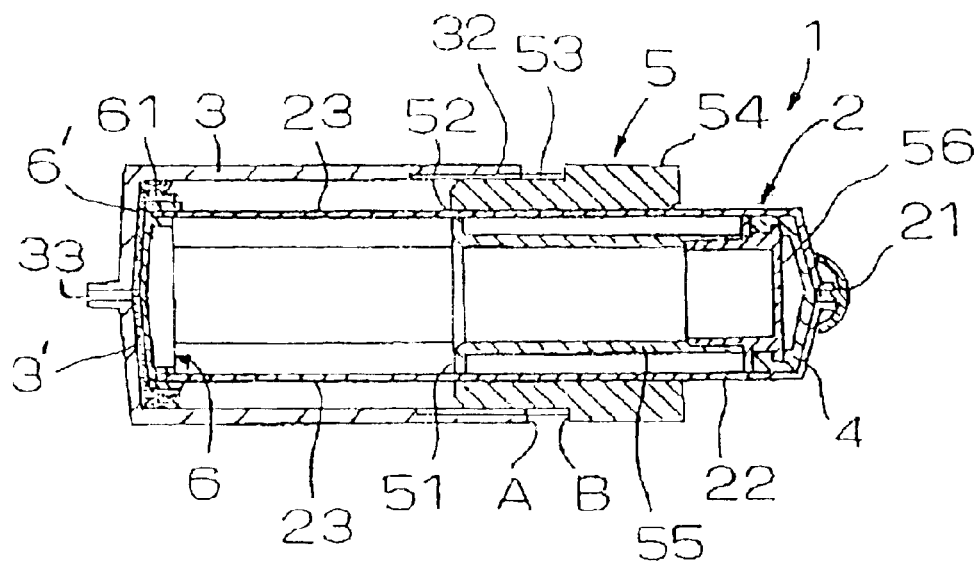
FIG. 1 is a front sectional view of a continuous liquid infusion device according to one embodiment of the present invention.

An end part A of the female screw part 32 and a bottom part B of the male screw part 53 are apart from each other with a predetermined distance as shown in FIG. 1 when the movable unit 6 liquid-tightly fitted on the inner surface of the tip of the liquid syringe 3 through the gasket 61 abuts against the base end side of the leg parts 23 of the negative pressure cylinder 2. Accordingly, turning the outer case 5 in a direction to fasten the liquid syringe 3 results in moving the negative pressure cylinder 2 to the piston 4 integrated with the outer case 5 between the end part A and the bottom part B. Since the piston 4 is integrated with the outer case 5 which does not move, an extra vacuum part C' is formed in the barrel part 22 of the tip of the negative pressure cylinder 2. On the other hand, turning the outer case 5 in a direction to loosen the liquid syringe 3 separates the outer case 5 and the liquid syringe 3.

Figure 7:
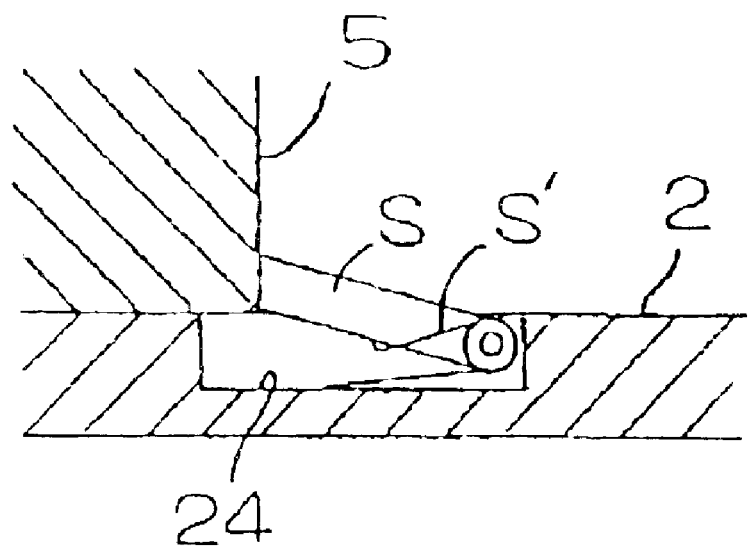
FIG. 7 is a partially enlarged sectional view showing that a stopper is formed in thickness of the negative pressure cylinder for using a liquid syringe into which liquid is previously infused.

It should be noted that in the continuous liquid infusion device according to the one embodiment of the present invention, the outer case 5 including the negative pressure cylinder 2 and the liquid syringe 3 are separable from each other so that an empty liquid syringe 3 can be exchanged to a liquid syringe into which liquid is infused in advance. Needles to say, when the latter (previously liquid-infused) liquid syringe is used, it is necessary to provide a stopper S in a concave 24 provided in the thickness of the negative pressure cylinder 2 so as to lock the stopper S with a part of the outer case 5 at a position where the negative pressure cylinder 2 is moved in a negative pressure direction as shown in FIG. 7. Incidentally, symbol "S'" in FIG. 7 denotes an energizing means for energizing the stopper S in a locking direction.

Figure 5:
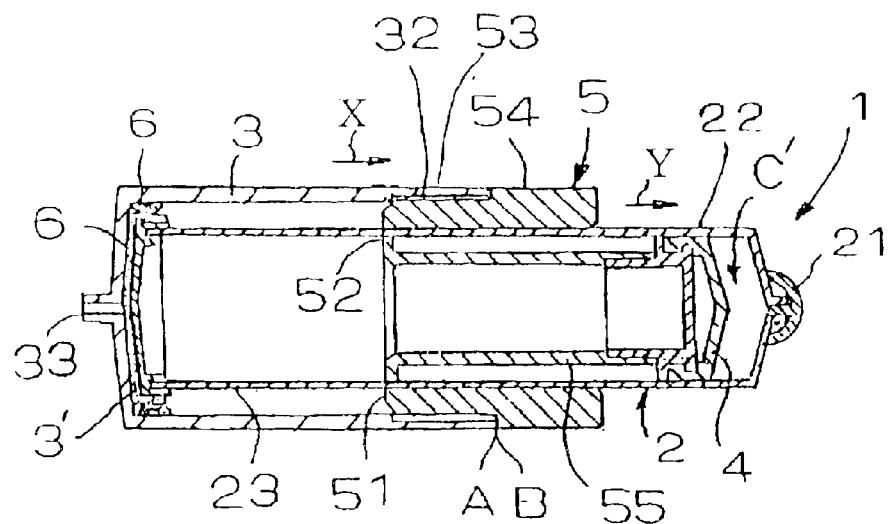
FIG. 5 is a front sectional view showing a state in which an extra vacuum part is created in the negative pressure cylinder of the continuous liquid infusion device according to the one embodiment of the present invention.
Figure 6:
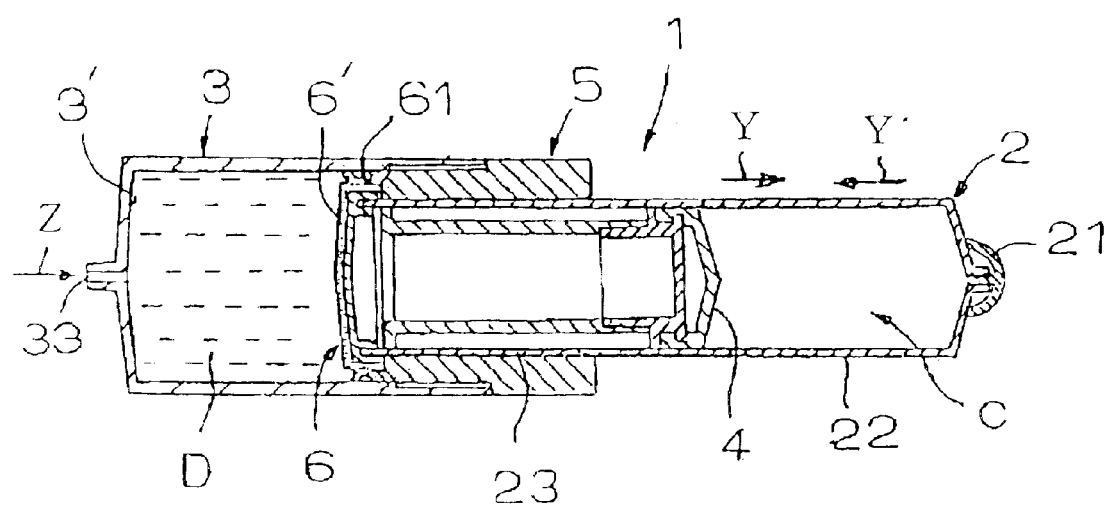
FIG. 6 is a front sectional view showing the time when liquid is completely infused into a liquid syringe of the continuous liquid infusion device according to the one embodiment of the present invention.

Next, the operation of the continuous liquid infusion device 1 according to the one embodiment of the present invention will be explained with reference to FIG. 1, FIG. 5, and FIG. 6. First, the liquid syringe 3 is held with one hand while the enlarged part 54 of the outer case 5 is held with the other hand, turning the enlarged part 54 in a direction to fasten the female screw part 32 of the liquid syringe 3 to the male screw part 53 of the outer case 5. This moves the liquid syringe 3 from a position in FIG. 1 in a direction shown by an arrow X in FIG. 5 so that the barrel part 22 of the negative pressure cylinder 2 is pushed out in a direction shown by an arrow Y through the leg parts 23. On the other hand, since the piston 4 in the negative pressure cylinder 3 integrated with the outer case 5 maintains its position (does not move), the extra vacuum part C' is formed in the barrel part 22 at the tip of the negative pressure cylinder 2. The outer case 5 moves until the end part A of the female screw part 32 of the liquid syringe 3 reaches the bottom part B of the male screw part 53 of the outer case 5.

Subsequently, liquid D is infused from the liquid infusion/discharge port 33 of the liquid syringe 3 in a direction shown by an arrow Z. As a result, the movable unit 6 further pushes out the barrel part 22 through the leg parts 23 of the negative pressure cylinder 2 in the direction of the arrow Y as the liquid accumulates between an end surface 3' in the tip end part of the liquid syringe 3 and an end surface 6' of the movable unit 6 having the gasket 61. Then, as shown in FIG. 6, when the liquid syringe 3 is filled up, a negative pressure C in the barrel part 22 of the negative pressure cylinder 2 is maximized.

Thereafter, connecting an instrument (not shown) connected to the liquid infusion/discharge port 33 of the liquid syringe 3 to a vessel or the like of a human body makes it possible to continuously infuse the liquid D in the liquid syringe 3 into the human body at regular speed and flow rate through the instrument since a negative pressure formed in relation with the piston 4 in the barrel part 22 of the negative pressure cylinder 2 moves the negative pressure cylinder 2 in a direction of an arrow Y' to press the gasket 61 of the movable unit 6. It should be noted that the total amount of the liquid D in the liquid syringe 3 is completely pushed out since the extra vacuum part C' is created before the infusion of the liquid D.

Next, in the continuous liquid infusion device according to the one embodiment of the present invention, a case will be explained in which the empty liquid syringe 3 is removed from the outer case 5 including the negative pressure cylinder 2 in a predetermined manner and the liquid syringe into which liquid is in advance infused is used. In this case, the maximum negative pressure C is created inside the negative pressure cylinder 2 by pressing hard a base end part of the leg parts 23 of the removed negative pressure cylinder 2 onto a desk or the like. The maximum negative pressure C is maintained by the operation of the stopper S. Then, the liquid infused liquid syringe 3 is screwed with the outer case 5. This state is equivalent to a filled-up liquid syringe 3 as shown in FIG. 6. As described above, therefore, when the instrument (not shown) connected to the liquid infusion/discharge port 33 of the liquid syringe 3 is connected to the vessel or the like of the human body and then the stopper S is released (pushed with a finger or the like into the concave 24) against the energizing means S', the liquid in the liquid syringe 3 is continuously infused into the human body at regular pressure by the gasket 61 of the movable unit 6 which is pressed by the negative pressure cylinder 2.

The invention is not limited to the above embodiments and various modifications may be made without departing from the spirit and scope of the invention. Any improvement may be made in part or all of the components.

What is claimed is:

1. A continuous liquid infusion device comprising:
    a negative pressure cylinder having a barrel part with an open/close valve at its tip and leg parts extending from a base end of the barrel part;
    a piston air-tightly fitted in the barrel part of said negative pressure cylinder and connected to a base end of an outer case through slots between the leg parts of said negative pressure cylinder, the outer case covering an outer surface of the barrel part;
    a liquid syringe having a liquid infusion/discharge port at its tip, and a base end screwed with the outer case so that said liquid syringe is positioned back to back with said negative pressure cylinder; and
    a movable unit liquid-tightly fitted to an inner circumference of the tip of said liquid syringe and abutting against a base end side of the leg parts of said negative pressure cylinder.

2. The continuous liquid infusion device according to claim 1, wherein
    the outer case is provided with an enlarged part as a handle in its outer circumference.

3. The continuous liquid infusion device according to claim 1, wherein
    said liquid syringe is removable from the outer case, and said negative pressure cylinder is provided with a stopper for fixing the outer case at a position where said negative pressure cylinder is moved in a negative pressure direction.

* * * * *